United States Patent [19]

Hanlon et al.

[11] 4,212,797

[45] Jul. 15, 1980

[54] SYNTHETIC PENTAPEPTIDE HAVING OPIATE AGONIST ACTIVITY

[75] Inventors: Brenton G. A. Hanlon, Palo Alto; Jaw-Kang Chang, San Jose; Bosco T. W. Fong, Sunnyvale, all of Calif.

[73] Assignee: Beckman Instruments, Inc., Fullerton, Calif.

[21] Appl. No.: 654,641

[22] Filed: Feb. 2, 1976

[51] Int. Cl.² ............... C07C 103/52; A61K 37/00
[52] U.S. Cl. ............................. 260/112.5 R; 424/177
[58] Field of Search ............... 260/112.5 R; 424/177

[56] References Cited

PUBLICATIONS

Hughes et al., Nature, 258, 577–579 (1975).

*Primary Examiner*—Delbert R. Phillips
*Attorney, Agent, or Firm*—Robert J. Steinmeyer; Robert S. Frieman

[57] ABSTRACT

A synthetic pentapeptide of opiate agonist activity having the formula H-Tyr-Gly-Gly-Phe-Met-$NH_2$ formed in a solid-state method.

1 Claim, No Drawings

SYNTHETIC PENTAPEPTIDE HAVING OPIATE AGONIST ACTIVITY

BACKGROUND OF THE INVENTION

A paper by Hughes et al entitled "Identification of Two Related Pentapeptides from the Brain with Potent Opiate Agonist Activity", Nature, 258, 577–579 (1975), reports the purification and identification of an endogenous substance from the extracts of pig brains termed "enkephalin" which acts as an agonist at opiate receptor sites. Hughes et al also report the enkephalin is comprised of two related pentapeptides (a) H-Tyr-Gly-Gly-Phe-Met-OH and (b) H-Tyr-Gly-Gly-Phe-Leu-OH (herein enkephalin sequence one and sequence two, respectively), in a ratio of approximately 3:1. Enkephalin is reported to be more potent than morphine, sequence one being more potent than sequence two. Both sequences have been synthesized and the synthetic pentapeptides illustrate similar opiate agonist effects to the naturally occuring substance.

SUMMARY OF THE INVENTION AND OBJECTS

In accordance with the present invention, a synthetic pentapeptide of the formula H-Tyr-Gly-Gly-Phe-Met-NH$_2$ (herein the subject pentapeptide) is provided having potent opiate agonist activity. The subject pentapeptide is structurally similar to enkephalin sequence one. The only modification is the substitution of an amine (—NH$_2$) at the C-terminus. This modification results in significantly improved potency compared to enkephalin.

It is an object of the present invention to provide a synthetic pentapeptide having highly potent opiate agonist activity in comparison to enkephalin. Further objects and features of the invention will be apparent from the following description.

DETAILED DESCRIPTION OF THE PREFERRED EMBODIMENTS

The present invention relates to the subject pentapeptide having opiate agonist activity. The present description will utilize conventional abbreviations for the amino acids in the peptide chains as follows: Tyrosine-Tyr; Glycine-Gly; Phenylalanine-Phe; and Methionine-Met. The peptide chain includes an N-terminal free alpha amino acid group and a C-terminal free carboxyl group substituted with an amide group. The formula of the subject pentapeptide will refer to the N-terminus as "H—" and to the amide substituted C-terminus as "—NH$_2$".

The subject pentapeptide of the present invention is preferably synthesized by a solid-state technique performed on a resin support. The general technique is disclosed by Stewart and Young in their book entitled "Solid-Phase Peptide Synthesis", (1969). The preferred technique is set forth in an article by Merrifield entitled "The Chemical Synthesis of Peptides and Proteins", published in Fractions, No. 2, by Spinco Division of Beckman Instruments, Inc., Palo Alto, California. The description of both sources relating to this solid-state technique is incorporated at this point by reference.

A general scheme for the formation of the subject pentapeptide is as follows:

In the first step, the first amino acid is anchored or attached to the solid support. As set forth in the aforementioned Merrifield article, a suitable solid support comprises small (e.g., 15 microns diameter) beads formed of a copolymer of styrene and 1% divinylbenzene forming a gel-like matrix of randomly coiled polystyrene cross-linked by divinylbenzene. When the beads are swollen, they contain about 80% solid and 20% styrene to form an open network of solvated polymer with relatively little resistance to diffusion of amino acids reagents.

The subject pentapeptide includes an amide group (—NH$_2$) at the C-terminus. A preferred support for this purpose is of the above polymeric type including a benzylester derivative, benzhydrylamine (BHA) resin. Such resins are commercially available consisting of white spherical beads. The amino groups of this resin attach to the carboxyl group of the first amino acid in the subject pentapeptide, methionine, and is relatively stable to synthesis conditions. However, cleavage by strong anhydrous acid after assembly of the peptide chain causes the amino group to be attached to the C-terminus as an amide.

In a less preferred alternative to the use of BHA resin, amminolysis must be performed to produce the C-terminal amide during cleavage by using a chloromethylated or hydroxymethyl resin. This latter procedure is time consuming and produces a relatively low yield of product.

Prior to attachment of the first amino acid of the peptide chain to the solid-support, the system is saturated with a suitable solvent such as trifluoroacetic acid (TFA) in methylene chloride to swell the resin. During this step, an antioxidant for methionine, such as indole, is added to the system.

Attachment of the C-terminal amino acid (methionine) to the solid support requires activation of either the C-terminal group of the amino acid or the resin. Normally, the resin is activated. With the BHA resin, this occurs by liberating the free amine form of the resin. This process is accomplished by washing the free resin hydrochloride salt (which is the state at which the resin is normally stored) with a 20 to 30% by volume solution of triethylamine in methylene chloride and then washing with a solution of methylene chloride. Suitably, about 25 ml solvent may be employed per gram of resin for each wash.

After the resin or the C-terminal amino acid is activated, the two are coupled together. A suitable coupling solution comprises dicyclohexylcarbodiimide (DCC) as the coupling reagent in a solvent of methylene chloride. As with the activating solvents, 25 ml of solvent per gram of resin may be employed for this purpose.

When the C-group (—COOH) of the amino acid is being attached to the resin or the end of the peptide chain on the solid-support, the N-group (—NH$_2$) must be protected. In other words, the N-group is inactivated during the coupling step as by attaching an inert chemical group to it for protection. The conventionally employed N-protecting groups are of the class of tert-butyloxycarbonyl groups (t-Boc groups) or their derivatives. Such groups are preferred N-protecting groups for each of the amino acids of the subject pentapeptide. Ordinary t-Boc amino acids are commercially available from many sources throughout the world. One source is the Protein Research Foundation of Osaka, Japan.

After the amino acid is coupled to the peptide chain or, as in the case of C-terminal amino acid, to the resin, the N-protecting group is removed to permit reaction with the next amino acid. A suitable washing solution for this purpose comprises a 33% solution of trifluoroacetic acid (TFA) in chloroform which saturates the resin and removes the protecting group.

After termination of the deprotection step, amino acid at the end of the peptide chain may include the TFA salt rather than a free N-group. Thus, it is necessary to neutralize this salt as by washing with a solution of triethylamine in methylene chloride. After neutralization, the next t-Boc amino acid is coupled to the peptide in the manner set forth above.

This cycle is repeated until the subject pentapeptide is grown.

The peptide chain is then cleaved from the solid support by a conventional cleavage technique. The preferred cleavage reagent is anhydrous hydrogen fluoride, which also simultaneously removes any protecting groups of side-chain functional units on the amino acids. These latter protecting groups are necessary for those amino acids which have more than two reacting groups other than the C-group and the N-group. The only amino acids in the subject pentapeptide which requires side-chain protection is tyrosine. The usual type of protection for the side-chain of such an amino acid is a benzyl or carbonate type group although others may be employed.

The subject pentapeptide may be formed on an automated solid apparatus for synthesizing peptides. A preferred apparatus is the Beckman Model 990 Peptide Synthesizer manufactured by the Spinco Division of Beckman Instruments, Inc., and described in Instruction Manual No. SY-IM-2 published December 1972.

After the cleavage step, the cleavage reagent is removed as by evaporation in vacuo and the dry mixture is washed with anhydrous ether prior to dissolution of the peptide in water. The resin is then filtered and rinsed with water to form a series of water extractions of crude peptide which are pooled and lyophilized.

The subject pentapeptide is then purified or isolated from the crude peptide extract. Suitably such purification is based on separation by solubility differences to remove inactive oxidized materials and other impurities. Examples of this separation are either counter-current distribution, liquid-liquid extraction, or partition column chromatography. A preferred purification method is counter-current distribution (CCD). A preferred solvent system is butanol:acetic acid:water (4:1:5).

Independent tests were performed comparing the potency of the subject pentapeptide with the two peptides enkephalin and with morphine following the general technique set forth in Pert, C. B., and Snyder, S., *Proceedings of the National Academy of Sciences*, Vol. 70, pp. 2243–2247 (1973). The potency is measured as $ID_{50}$, defined as the concentration required to inhibit 50% of stereospecific naloxone binding. The results are set forth in the following table. The concentration of sodium was 100 mM. The effectiveness is inversely related to the $ID_{50}$ value.

Table 1

| Compound | $ID_{50}$ |
| --- | --- |
| Morphine | 0.2 |
| Enkephalin sequence one (H-Tyr-Gly-Gly-Phe-Met-OH) | 0.4 |
| Enkephalin sequence two (H-Tyr-Gly-Gly-Phe-Leu-OH) | 1.4 |
| Subject Pentapeptide | 0.2 |

Table 1-continued

| Compound | $ID_{50}$ |
| --- | --- |
| (H-Tyr-Gly-Gly-Phe-Met-NH$_2$) | |

It is apparent from the above table that the subject pentapeptide is twice as potent as the more potent sequence of enkephalin. This marked increase in potency is totally unexpected.

The subject pentapepide has a wide variety of potential uses, e.g., as an analgesic, a muscle relaxant, or a sedative. It can be delivered for treatment in dosage effective quantities by the use of a suitable carrier. For example, it can be injected into the patient's system in a suitable solvent such as an isotonic solution. Also, it can be atomized in solution as into the bronchial passages. Furthermore, it can be encapsulated with a standard inert dry powder diluent carrier such as lactose.

A further disclosure of the nature of the present invention is provided by the following specific example of the practice of the invention. It should be understood that the data disclosed serve only as an example and is not intended to limit the scope of the invention.

EXAMPLE

The subject pentapeptide (H-Tyr-Gly-Gly-Phe-Met-NH$_2$) is synthesized by a solid-state method on a Beckman Model 990 Peptide Synthesizer. The process is run automatically by programming the instrument. The following t-Boc amino acids are sequentially coupled together to form the present pentapeptide:

Boc-L-Methionine
Boc-L-Phenylalanine
Boc-L-Glycine
Boc-O-(o-Bromocarbobenzoxy)-L-Tyrosine It is apparent that only the tyrosine requires side-chain protection. The foregoing amino acid derivatives are coupled together in the sequence of the present pentapeptide by the following procedure:

Dry BHA resin (made by Beckman Instruments, Inc.—Catalog No. 338684) is placed in the reaction vessel and prewashed with a solution of methylene chloride including 10% triethylamine (TEA). This saturates the system with the solution and swells the resin. Then the resin is washed three times with chloroform to activate the resin by removing its hydrochloride salt.

The Boc derivative of the C-terminus amino acid (methionine) is then coupled with a 2.5 molar excess of DCC. The Boc-methionine (2.5 molar excess for one equivalent of resin) is dissolved in a suitable solvent such as dimethyl formamide (DMF) or methylene chloride. Thereafter, the following cycle is repeated for each subsequent amino acid, in order, phenylalanine, glycine, glycine, tyrosine.

Removing the N-protecting Group

Wash with 33% TFA in methylene chloride to remove the t-Boc protective group by stirring for 20 minutes;

Wash with chloroform to remove the TFA from the previous step;

Wash with 33% dioxane in methylene chloride to remove any residual TFA;

Wash with methylene chloride to remove remaining dioxane.

Neutralization of any TFA Salt Formed

Wash with 10% triethylamine (TEA) in methylene chloride to neutralize the TFA salt formed during removal of the t-Boc protective group.

Coupling Next Amino Acid onto the Peptide Chain

Wash 3 times with methylene chloride to remove any remaining TFA salts;

Dissolve the next Boc-amino acid in DMF or methylene chloride (2.5 equivalent of Boc-amino acid for 1 equivalent of resin) and introduce the same to the reaction vessel;

Add 2.5 M excess of DCC in methylene chloride and permit the coupling reaction to proceed for two hours or until completion; and Wash two times with methylene chloride to remove excess unreacted amino acid, DCC, and reaction by-products from the reaction vessel prior to commencing the next cycle.

Cleavage of Peptide from Resin

When all of the amino acids have been coupled by the above step-wise procedure, in a cleavage step, the completed peptide is removed from the resin, the Boc is removed from the N-terminal amino acid, and the side-chain protecting groups are removed. Suitably this is accomplished as follows:

The completed protected peptide resin is washed sequentially with the following solvents: (a) 33% TFA/methylene chloride/1% indole, (b) chloroform, (c) methylene chloride, and (d) methanol;

The material is dried in vacuo;

The peptide resin is stirred for one hour at 0° C. and hydrofluoric acid (HF) in a proportion of 10 ml/gram of resin, containing 10% anisole and 0.5% 2-mercapto ethanol, to cleave the peptide from the resin support and remove the side chain protecting groups;

The reaction chamber is subjected to a vacuum to remove the HF by evaporation;

The dry reaction mixture is washed with anhydrous ether;

The peptide is dissolved in water;

The resin is filtered off and rinsed with water; and

The water extractions are pooled and lyophilized.

Purification

The crude peptide is then purified as follows:

The peptide is isolated from the lyophilized crude extract by partition chromatography in a column containing Sephadex G-25 Fine beads manufactured by Pharmacia Fine Chemicals. A solvent system of butanol:acetic acid:water (4:1:5) is employed.

The subject pentapeptide formed in the foregoing manner has an opiate agonist activity set forth in the foregoing table.

What is claimed is:

1. A synthetic pentapeptide with opiate agonist activity having the formula H-Tyr-Gly-Gly-Phe-Met-NH$_2$.